United States Patent [19]

Irr et al.

[11] Patent Number: 5,108,760
[45] Date of Patent: Apr. 28, 1992

[54] ENHANCES LAK CELL ACTIVATION BY TREATMENT OF HUMAN PERIPHERAL BLOOD MONONUCLEAR CELLS WITH AMINO ACID AMIDES

[75] Inventors: Joseph D. Irr, Newark, Del.; Kam Leung, Brookhaven, Pa.

[73] Assignee: Terumo Corporation, Tokyo, Japan

[21] Appl. No.: 383,221

[22] Filed: Jul. 21, 1989

[51] Int. Cl.$^5$ .............................. A61K 35/14; C12N 5/08
[52] U.S. Cl. .................................... 424/534; 424/529; 424/577; 424/578; 424/9; 424/85.1; 424/85.2; 435/240.1; 435/240.2; 435/240.21; 435/240.25; 435/948; 514/21; 514/885
[58] Field of Search ............ 424/85.1, 85.2, 101, 424/9, 529, 534, 577–578; 530/351; 435/240.1, 240.2, 240.21, 240.25, 948; 514/21, 885

[56] References Cited

U.S. PATENT DOCUMENTS 4,690,916  9/1987  Rosenberg ........................ 424/85.2
4,849,329  7/1989  Leuny et al. ........................ 514/2

OTHER PUBLICATIONS

Shaw et al., *Cancer Immunol. Immunother,* 27, 1988, pp. 255–260.
Mills et al. *The Journal Immunol* 125 (5) 1980, pp. 1904–1909.
McCrady et al., *Cancer Res* 48, 1988, pp. 635–640.
Eggermont et al., *Br. J. Cancer* 58, 1988, pp. 410–414.
McCrady et al., *Lymphokine Res* 6(1) 1987, pp. 45–57.

*Primary Examiner*—Garnette D. Draper
*Attorney, Agent, or Firm*—Burns, Doane, Swecker & Mathis

[57] ABSTRACT

There is provided an improved process for enhanced LAK cell activation wherein the peripheral blood mononuclear cells are treated with an amino acid amide to yield depletion, prior to the lymphocytes being cultured at high density. Also provided are pharmaceutical compositions and methods of using them in combination with IL-2 to treat cancer in a mammal.

29 Claims, No Drawings

ENHANCES LAK CELL ACTIVATION BY TREATMENT OF HUMAN PERIPHERAL BLOOD MONONUCLEAR CELLS WITH AMINO ACID AMIDES

FIELD OF THE INVENTION

This invention relates to the generation of cells having enhanced lymphokine-activated killer (LAK) cell activity which are useful in adoptive immunotherapy.

BACKGROUND OF THE INVENTION

Incubation of interleukin-2 (IL-2) with human peripheral blood mononuclear cells (PBMC) or mouse splenocytes induces a population of highly tumoricidal cells. This phenomenon has been referred to as lymphokine-activated killer (LAK) cell activity. The precursor of the LAK effector cells may be heterogeneous, but most of the activity apparently originates from large granular lymphocytes (LGL) which comprise about 5% of peripheral blood lymphocytes (PBL) and which have natural killer (NK) cell activity.

Adoptive transfer of LAK cells to tumor-bearing mice with simultaneous administration of IL-2, has resulted in reduction in tumor burden in several animal models. From these results clinical trials were developed utilizing LAK cells alone. IL-2 alone, and finally an intensive treatment program utilizing both agents in patients with advanced solid tumors (Rosenberg et al., (1987) N. Engl. J. Med. 316:889-897: U.S. Pat. No. 4,690.915 issued to Rosenberg). The toxicity of this combination regimen was considerable despite the fact that Rosenberg was able to deliver in man only 1 to 10% of the equivalent dose compared to the effective murine doses of LAK cells and IL-2 (based on weight). Nevertheless, a significant number of partial responses were seen and further trials of the combination of IL-2 and LAK cells are underway.

Central to the problem of the utilization of LAK cells in man is the complexity of their generation (also referred to herein as induction or activation): patients are leukapheresed, the leukapheresis product is separated by Ficoll-Hypaque gradients, and the resultant mononuclear cells are then cultured in the presence of IL-2 at cell densities of 1 to $3 \times 10^6$ cells per mL for 3 to 5 days. Thus, the final culture volumes in roller bottles can reach 40 L. Various changes and improvements have been made in this procedure. For example, European patent application 87107755.8, published Dec. 2, 1987, and co-assigned, allowed U.S. patent application 07/038361, filed Apr. 20, 1987, now U.S. Pat. No. 4,849,329 disclose that depletion of monocytes by exposure of mononuclear cells to phenylalanine methyl ester (PME) allows LAK cell induction at cell culture densities about 10-fold greater than the currently utilized LAK cell induction concentrations. European patent application 88101138.1, published Aug. 31, 1988 and pending, co-assigned U.S. patent application 07/008273, filed Jan. 29, 1987, disclose that LAK cell induction can be carried out in bags made of organic polymeric, oxygen permeable film. European patent application 88106566.8 published Nov. 9, 1988, and co-assigned U.S. Pat. No. 4,808,151, issued February 28, 1989, disclose that the leukapheresis product need not be separated on a Ficoll-Hypaque gradient prior to use in the activation process.

Incubating mixtures of human white blood cells collected from the peripheral blood by venipuncture or leukapheresis with esters of various amino acids leads to the transient or permanent loss of functional natural killer (NK) cells (Thiele et al. (1985) Proc. Natl. Acad. Sci. USA 82:2468-2472: U.S. Pat. No. 4,752,602 issued to Lipsky and Theile). With the methyl ester of leucine (LME), a dipeptide leucyleucine methyl ester is formed in cells exposed to LME, which is toxic to the NK cells (Thiele et al. (1985) Proc. Acad. Sci. USA 82:2468-2472: U.S. Pat. No. 4,752,602). The use of PME and other lower alkyl amino acid esters, including the esters of alanine, aspartic acid, cysteine, glutamic acid, glutamine, phenylalanine, proline, tyrosine, tryptophan, and valine, or a mixture of any of the foregoing, in a process to prepare LAK cells is disclosed in European patent application 87107755.8, published Dec. 2, 1987, and allowed U.S. application 07/038361. filed Apr. 20, 1987, now U.S. Pat. No. 4,849,329. A problem still exists with the processes described in the art due to the complexity and high volume of the induction or activation systems needed for human LAK cell immunotherapy. The present application describes a process for LAK cell activation at high cell density therefore rendering murine equivalent doses of LAK cell therapy in humans as a feasible alternative.

SUMMARY OF THE INVENTION

This invention relates to enhanced lymphokine-activated killer (LAK) cell activation and more particularly to an improved process for LAK cell activation. In the process wherein peripheral blood mononuclear cells (PBMC) are cultured to produce a population of cells which are cytotoxic for fresh tumor cells, the improvement comprises contacting the PBMC or peripheral blood lymphocytes (PBL) resulting therefrom. prior to culturing said cells at high density, with an L-amino acid amide, wherein the L-amino acid is selected from the group consisting of leucine, isoleucine, phenylalanine, and valine, or a mixture of any of the foregoing, and thereafter culturing the resulting cells.

Also provided in the present invention are improved compositions comprising isolated LAK cells prepared by the foregoing process, said cells being dispersed in a pharmaceutically acceptable carrier and being reactive to tumor when administered with interleukin-2 to a human afflicted with said tumor.

Further provided are methods for treating cancer in a mammal comprising administering to the mammal interleukin-2 (IL-2) and a tumor-inhibiting amount of the improved compositions of this invention.

Furthermore, the present invention relates to improved processes, compositions, and methods of use described above, wherein an L-amino acid amide is used in combination with an L-amino acid lower alkyl ester.

This application describes the use of L-amino acid (aa) amides and preferably L-phenylalaninamide (PAA) for the removal of monocytes, prior to the incubation of the lymphocytes with IL-2 for the production of LAK cells in high cell density cultures. As used herein "high cell density" means cell densities where there is an inhibition of LAK cell production with respect to that obtained in a culture of lower cell density: "high cell density" means cell density greater than about $3 \times 10^6$ cells/mL to about $1 \times 10^8$ cells/mL and preferably $1 \times 10^7$ cells/mL. For PBMC from certain donors, PAA appears to enhance the extent of LAK cell activation at high cell density compared to the activation obtained by treatment with L-phenylalanine methyl ester (PME) of the same batch of human cells.

Thus, we have developed a practical process to augment the number of LAK cells available for human LAK cell therapy and simultaneously reduce the complexity and volume of the induction system, so that murine equivalent doses of LAK cell therapy are now feasible in man.

The effect of aa amides on LAK cell generation at high cell density does not correlate with the effect of the corresponding aa alkyl ester. For example, the L-amino acid lower alkyl ester of aspartic acid, glutamic acid, and tyrosine enhances generation of LAK cells at high cell density (European patent application 87107755.8. published Dec. 2, 1987 and allowed U.S. patent application 07/038361, filed Apr. 20, 1987), whereas the corresponding aa amide of these amino acids did not function to enhance LAK cell generation (Example 5, Table 8). Moreover, some aa alkyl esters, including leucine and isoleucine methyl ester, do not enhance LAK cell generation at high cell density (European patent application 87107755.8, published Dec. 2, 1987 and allowed U.S. patent application 07/038361, filed Apr. 20, 1987), whereas the corresponding aa amides of these amino acids were found to enhance LAK cell production when the cells are cultured at high cell density (Example 5, Table 8).

Although all of the 20 possible amino acid amides have not been tested, it is expected that some of these aa amides, in addition to leucine, isoleucine, phenylalanine, and valine will be useful for enhancing the production of LAK cells when the cells are cultured at high cell density.

DETAILED DESCRIPTION OF THE INVENTION

LAK cell activation can be achieved by culturing lymphocytes from the peripheral blood with IL-2 or recombinant IL-2 (rIL-2) if the cell concentration is limited to $3 \times 10^6$/mL, even when there are numerous red blood cells (RBC) present, as disclosed by Dunn, Halpern and Irr in co-assigned U.S. Pat. No. 4,808,151, issued Feb. 28, 1989. When the monocytes are removed from such a preparation of mononuclear cells by chemical or physical means, such as with PME treatment or adherence to surfaces, and the RBC are removed by gradient separation, then the remaining lymphocytes may be cultured at densities of at least $1 \times 10^7$/mL (European patent allowed U.S. application 07/038361, filed Apr. 20, 1987).

In the process of this invention the PBMC are exposed to a salt of an L-amino acid amide at about room temperature for about 40 minutes in a phosphate buffered saline solution, pH 7.0 (PBS), containing 0.5% human serum albumin (Albuminar-25, Armour Pharmaceutical Co., Kankakee, IL). The optimum duration of treatment and temperature at which the cells are treated may be varied and will depend, for example, on the concentration of aa amide used. Other buffered solutions compatible with cell viability may also be used. This treatment results in destruction of monocytes present in the PBMC mixture. The remaining lymphocytes from the treated PBMC are isolated by Ficoll-Hypaque density gradient separation. The isolated cells are washed with PBS and then resuspended in a suitable cell culture medium, such as AIM-V (available from Gibco, Inc., Grand Island, NY). Other suitable media are well known and may be used in place of AIM-V, and are optionally supplemented with human or fetal calf serum for subsequent LAK cell activation.

A preferred embodiment of this invention provides for exposing the PBMC to the hydrochloride salt of L-phenylalaninamide (PAA) at room temperature for about 40 minutes in PBS, pH 7.0 containing 0.5% human serum albumin. The PAA may be present in a concentration of about 1 to 10 mM and preferably is present in a concentration of about 10 mM.

A further embodiment of this invention provides for exposing the PBMC to a combination of an L-amino acid amide and an L-amino acid lower alkyl ester. Preferably the combination used is PAA present in a concentration of about 1 to 10 mM and PME present in a concentration of about 1 to 5 mM.

Once the isolated lymphocytes are counted by standard laboratory methods, for example, using a hemacytometer and microscope, they are diluted to the desired concentration with AIM-V medium and placed in an appropriate cell culture container to be cultured at high densities. The preferred container is the SteriCell TM container, a gas permeable plastic bag commercially available from E. I. du Pont de Nemours & Co., Wilmington, DE. However, other gas permeable bags known in the art may be used. To achieve LAK cell activation, the cells are incubated with rIL-2 for three days at 37° C., 5% $CO_2$ and 95% relative humidity. Following the three days of incubation, LAK cell activity may be evaluated by testing portions of the cells in a cytotoxicity assay.

Cytotoxicity Assay

In the following examples, a 4-hour $^{51}Cr$ release assay was used to measure cytotoxic activity of LAK cell preparations. The targets used (Raji and Daudi cell lines) are human tumor cell lines well known for their relative insensitivity to NK cell-mediated cytotoxicity, but susceptibility to LAK cell-mediated cytotoxicity. The tumor target cells at a concentration of about $2 \times 10^6$ to $1 \times 10^7$ per mL were incubated with 100 µCi of $Na_2^{51}CrO_4$ in 0.4 mL of Tris-phosphate buffered saline for 1 hour at 37° C. The cells were washed three times with RPMI-1640 cell culture medium (Whittaker Bioproducts, Walkersville. MD) containing 10% fetal calf serum (FCS), and resuspended to $10^5$ cells per mL in RPMI-10% FCS. The effector cells (LAK cells) were resuspended to various concentrations in RPMI-10% FCS and 0.1 mL portions were placed into round bottom wells in microtiter plates. The $^{51}Cr$-labeled tumor target cells (0.1 mL) were added to all wells. After 4 hours incubation at 37° C., the plates were centrifuged and 0.1 mL of resulting supernatant fluid was removed from each well and counted in a gamma counter results are expressed in counts per minute (CPM). Each sample of LAK cells was tested in triplicate and the resulting data are expressed as % cytotoxicity.

Percent cytolysis is calculated from the following formula:

$$\% \text{ cytolysis} = \frac{\text{experimental } CPM - \text{spontaneous } CPM}{\text{total } CPM - \text{spontaneous } CPM} \times 100$$

This cytotoxicity test is widely used and is further described in *Selected Methods in Cellular Immunology*, Mishell and Shiigi, eds. 124–137, W. H. Freeman and Co., San Francisco, CA (1980). In some of the experiments the results of the assays are presented as lytic units (LU or $LU_{30}$). One lytic unit is defined as $10^6$ divided by the number of effector cells required to lyse 30% of the target cells. This value is computed from fitting a model wherein the % cytolysis is a function of the logarithm of the effector:target ratio. This calculation is based upon the method described by Pross et al., *J. of Immunological Methods* 68:35–249 (1984).

Cells: Human peripheral blood cells were collected from healthy donors on the Haemonetics V50 instrument by means of standard cytapheresis protocols as described in U.S. Pat. Nos. 4,464,167 and 4,416,654. Raji and Daudi cell lines were maintained in continuous culture by standard laboratory procedures; these cell lines were used as the tumor targets in the $^{51}Cr$ release assays.

Materials:

A. Media: The culture medium used for LAK cell activation consisted of AIM-V TM serum free medium with L-glutamine, streptomycin sulfate and gentamicin sulfate (Gibco). The medium used for culture of cell lines and $^{51}Cr$ release assays was RPMI-1640 with L-glutamine (Gibco) and 10% heat inactivated fetal bovine serum and 0.05 mcg/ml gentamicin sulfate.

Dulbecco's Phosphate-Buffered Saline without $Ca++$, $Mg++$ or Phenol red (PBS) (Gibco) was used for monocyte depletion with L-aa amides and/or L-aa lower alkyl esters and also for cell washing.

B. 50 mM PME Reagent: One gram of L-phenylalanine methyl ester, HCl (Du Pont) was added to 100 ml of PBS and 2 ml of human albumin (Albumina ®-25 U. S. P. 25%). The pH was adjusted to 7.0 with 0.1 N NaOH (Sigma).

C. 50 mM PAA Reagent: One gram of L-phenylalaninamide, HCl (Sigma) was added to 100 ml PBS and 2 ml of Albuminar ®-25 U.S.P 25%. The pH was adjusted to 7.0 with 0.1 N NaOH.

Other materials used are the same as those described in co-assigned U.S. Patent 4,808,151.

Procedure:

A. Collection of donor cells were by leukapheresis, using methods identical to those described in co-assigned U.S. Pat. No. 4,808,151.

B. Before further processing a sample of the leukapheresis product was removed for analysis. The remainder was placed in a centrifuge and spun at 468xg for 10 minutes for plasma and platelet separation and removal. The cell fraction was counted for white blood cells (WBC) and adjusted to a density of $1 \times 10^7$/mL with PBS supplemented with 0.5% human serum albumin. Portions of the cell suspension were treated with various concentrations of PAA from about 1 to 10 mM or mM PME for 40 minutes at room temperature and then were fractionated by the lymphocyte separation procedure.

C. Lymphocyte Separation: Forty mL of the blood cell suspension were underlaid with 10 mL of lymphocyte separation media (Ficoll-Paque, Pharmacia Fine Chemicals or Lymphoprep, Nycomed). The mixture was then centrifuged for 15 minutes at 800xg. After centrifugation, the resulting interface layer of mononuclear cells was collected and washed twice with PBS. The cells were washed a third time with AIM-V medium and a WBC count was performed.

D. Culturing Cells in Du Pont Stericell TM Containers. Cells were diluted to a density of $1 \times 10^7$/mL in AIM-V medium. Du Pont rIL-2, 100 units/mL, was added and the cultures were transferred into Stericell TM containers. These bags of cells were placed in a 37° C. incubator with 5% $CO_2$ and 95% RH for 3 or 4 days.

E. In vitro cytotoxicity assay.

Target cell preparation. The day preceding the assay, exponentially growing target cells were diluted to $1 \times 10^5$/mL in 10 mL of assay medium. On the assay day, $4 \times 10^6$ cells were washed and resuspended in 0.1 mL 2×TD buffer and 100 microCi $^{51}CrO_4$. The cells were incubated one hour at 37° C., washed twice, counted and diluted to $1 \times 10^5$/mL in assay medium.

Effector cell preparation. About 10 mL of the effector cell culture was washed twice with assay medium, counted and tested for viability. The cells were diluted to $4 \times 10^6$/mL in assay medium. Effectors and targets were mixed at ratios of 40:1, 20:1, 10:1, 5:1 and 2.5:1 in 96 well microtiter plates where they were incubated at 37° C. for 4 hours before the supernatant fractions were analyzed for $^{51}Cr$ content in a gamma counter.

EXAMPLES

Example 1

The effectiveness of L-phenylalaninamide, HCl (PAA) on human monocyte depletion and LAK cell activation in high cell density cultures was examined. PAA and other aa amides were obtained from Sigma. St. Louis. MO. For comparative purposes L-phenylalanine methyl ester. HCl (PME) treatments were also performed with aliquots of cells from each preparation of freshly donated human cells.

Sufficient cells were obtained from a donor (designated donor 1) to compare monocyte depletion and high density LAK cell activation in two preparations, one of which was treated with 5 mM PAA, and the other with 5 mM PME. Monocyte depletion was studied by standard hematological differential staining (Table 1A) and by FACS analysis (Table 1B). Smears or cytospins were exposed to Giemsa stain before they were evaluated by light microscopy. A fluorescent-activated cell sorter (FACS) and a panel of conjugated antibodies specific for human cell surface markers were used to quantify the various cell types: these antibodies. Leu4, Leu12, LeuM3, and Leu19, were obtained from Bectin Dickinson, Mountain View, CA. As shown, the samples treated with 5 mM PAA and 5 mM PME lost existing monocytes and were, thereby, enriched for lymphocytes.

TABLE 1A

| | Donor 1: Differential Staining | | |
|---|---|---|---|
| Sample | Lymphocytes | Monocytes | Granulocytes |
| Untreated | 67 | 32 | 1 |
| 5 mM PAA Treated | 99 | 1 | 0 |
| 5 nM PME Treated | 91 | 9 | 0 |

TABLE 1B

| | Donor 1: FACS Analysis | | | |
|---|---|---|---|---|
| Sample | Leu4* | Leu12* | LeuM3* | Leu19* |
| Untreated | 61 | 10 | 27 | 11 |
| 5 mM PAA Treated | 81 | 7 | 1 | 9 |
| 5 nM PME Treated | 80 | 13 | 5 | 9 |

Leu4* = T Lymphocytes
Leu12* = B Lymphocytes
LeuM3* = Monocytes
Leu19* = NK cells The PAA- and PME-treated cells were assayed for LAK cell activity against the two tumor cell targets, Raji and Daudi, following three days of culture in 48 mL of rIL-2- supplemented AIM-V medium in Steri-Cell ™ containers (Table 1C). The overall yields of cells from both treatments yielded greater than 100% recovery from the cultures. These cytolytic activities show that for this particular donor cell preparation greater LAK cell activation was obtained with cells exposed to 5.0 mM PAA than in those treated with 5.0 mM PME.

TABLE 1C

| | Donor 1: LAK Activity | | | | |
|---|---|---|---|---|---|
| | | % Cytolysis | | LU30 | |
| Sample | E:T Ratio | Raji | Daudi | Raji | Daudi |
| 5 mM PAA | 40:1 | 54.6 | 67.2 | 13.8 | 15.8 |
| | 20:1 | 46.6 | 46.9 | | |
| | 10:1 | 32.8 | 34.5 | | |
| | 5:1 | 26.9 | 28.2 | | |
| | 2.5:1 | 13.1 | 14.4 | | |
| 5 mM PME | 40:1 | 44.9 | 60.7 | 9.3 | 12.7 |
| | 20:1 | 34.6 | 48.3 | | |
| | 10:1 | 34.1 | 28.3 | | |
| | 5:1 | 22.3 | 19.7 | | |
| | 2.5:1 | 9.4 | 13.9 | | |

Example 2

The effects of varied concentrations of PAA on the activation of human LAK cell in high density culture was examined. Again, 5 mM PME treatment of an aliquot of the cells was included as an internal control of the study.

The cells from a leukapheresis collection from donor 2, designated donor 2 cells, were divided into six portions for treatment with PAA at various concentrations, a 5 mM PME control and an untreated control. Differentials and FACS analyses were run on specimens after treatment and the remaining cells were cultured for LAK cell activation, as with donor 1 cells (Example 1). The results obtained using donor 2 cells are given in Tables 2A, 2B, and 2C. The extent of monocyte depletion was similar in all of the chemically treated samples. The extent of LAK cell activation was related to the concentration of PAA used. As shown in Table 2C, the optimum PAA concentration for LAK generation was 10 mM and PAA appeared to be somewhat more effective than 5 mM PME for LAK cell generation, for cells from donor 2. 5 mM is the known optimum concentration for PME (see, for example, Table 6).

TABLE 2A

| | Donor 2: Differential Staining | | |
|---|---|---|---|
| Sample | Lymphocytes | Monocytes | Granulocytes |
| Untreated | 76 | 22 | 2 |
| 5 mM PAA Treated | 90 | 9 | 1 |
| 10 mM PAA Treated | 90 | 6 | 4 |
| 15 mM PAA Treated | 91 | 5 | 4 |
| 20 mM PAA Treated | 87 | 8 | 7 |
| 5 mM PME Treated | 95 | 4 | 1 |

TABLE 2B

| | Donor 2: FACS Analysis | | | |
|---|---|---|---|---|
| SAMPLE | Leu4* | Leu12* | LeuM3* | Leu19* |
| Untreated | 75 | 10 | 18 | 9 |
| 5 mM PAA Treated | 73 | 6 | 8 | 5 |
| 10 mM PAA Treated | 76 | 8 | 6 | 5 |
| 15 mM PAA Treated | 77 | 8 | 5 | 5 |
| 20 mM PAA Treated | 78 | 7 | 5 | 4 |

TABLE 2B-continued

| | Donor 2: FACS Analysis | | | |
|---|---|---|---|---|
| SAMPLE | Leu4* | Leu12* | LeuM3* | Leu19* |
| 5 mM PME Treated | 75 | 7 | 7 | 6 |

Leu4* = T Lymphocytes
Leu12* = B Lymphocytes
LeuM3* = Monocytes
Leu19* = NK cells

TABLE 2C

| | Donor 2: LAK Activity | | | | |
|---|---|---|---|---|---|
| | | % Cytolysis | | LU30 | |
| Sample | E:T Ratio | Raji | Daudi | Raji | Daudi |
| Untreated | 40:1 | 7.7 | 17.6 | | |
| | 20:1 | 2.8 | 0.7 | | |
| | 10:1 | 11.3 | 7.9 | 0 | 0 |
| | 5:1 | 5.0 | 6.7 | | |
| | 2.5:1 | 2.8 | 5.1 | | |
| 5 mM PAA | 40:1 | 43.1 | 38.1 | | |
| | 20:1 | 36.6 | 28.5 | | |
| | 10:1 | 8.1 | 4.9 | 5.2 | 3.4 |
| | 5:1 | 7.0 | 4.0 | | |
| | 2.5:1 | 9.0 | 5.7 | | |
| 10 mM PAA | 40:1 | 57.9 | 44.4 | | |
| | 20:1 | 43.9 | 39.2 | | |
| | 10:1 | 39.3 | 30.4 | 11.5 | 7.6 |
| | 5:1 | 22.5 | 13.3 | | |
| | 2.5:1 | 0 | 0 | | |
| 15 mM PAA | 40:1 | 19.1 | 8.8 | | |
| | 20:1 | 16.9 | 9.4 | | |
| | 10:1 | 10.2 | 4.5 | 0.5 | 0 |
| | 5:1 | 7.0 | 5.2 | | |
| | 2.5:1 | 2.8 | 4.2 | | |
| 20 mM PAA | 40:1 | 31.7 | 21.8 | | |
| | 20:1 | 14.6 | 7.4 | | |
| | 10:1 | 18.6 | 12.6 | 1.6 | 0.2 |
| | 5:1 | 10.6 | 6.9 | | |
| | 2.5:1 | 8.9 | 4.4 | | |
| 5 mM PME | 40:1 | 48.0 | 52.6 | | |
| | 20:1 | 40.6 | 37.9 | | |
| | 10:1 | 7.4 | 7.1 | 6.1 | 6.3 |
| | 5:1 | 5.0 | 4.4 | | |
| | 2.5:1 | 6.2 | 7.5 | | |

Cells from two other donors, designated donors 3 and 4, were used to further examine the effects of varied concentrations of PAA on LAK cell activation. The results obtained using donors 3 and 4 cells are given in Tables 3A, 3B, 3C, 4A, 4B, and 4C. With these cells, lower concentrations of PAA were tested before the high density activation step. In both cases there was a concentration dependent effect on the LAK cell activation response. This dependence upon PAA for efficient LAK cell activation was particularly noticeable in these samples because the untreated cells failed to produce LAK cell activity. The PME-treated cells from donor 4 were not active in the LAK cell assays whereas, PAA did enhance LAK activity in donor 4 cells (Table 4C). The results suggest that, in some donors, a greater level of LAK activity may be obtained using PAA than can be obtained using PME.

TABLE 3A

| | Donor 3: Differential Staining | | |
|---|---|---|---|
| Sample | Lymphocytes | Monocytes | Granulocytes |
| Untreated | 71 | 28 | 1 |
| 0.5 mM PAA Treated | 74 | 26 | 0 |
| 2.5 mM PAA Treated | 86 | 14 | 0 |
| 5 mM PAA Treated | 92 | 7 | 1 |
| 10 mM PAA Treated | 95 | 5 | 0 |
| 5 mM PME Treated | 93 | 4 | 3 |

TABLE 3B

| | Donor 3: FACS Analysis | | | |
|---|---|---|---|---|
| SAMPLE | Leu4* | Leu12* | LeuM3* | Leu19* |
| Untreated | 75 | 13 | 18 | 12 |
| 0.5 mM PAA Treated | 80 | 14 | 19 | 7 |
| 2.5 mM PAA Treated | 81 | 12 | 10 | 7 |
| 5 mM PAA Treated | 83 | 15 | 6 | 16 |
| 10 mM PAA Treated | 79 | 13 | 7 | 13 |
| 5 mM PME Treated | 70 | 12 | 6 | 10 |

Leu4* = T Lymphocytes
Leu12* = B Lymphocytes
LeuM3* = Monocytes
Leu19* = NK cells

TABLE 3C

| | | Donor 3: LAK Activity | | | |
|---|---|---|---|---|---|
| | | % Cytolysis | | LU30 | |
| Sample | E:T Ratio | Raji | Daudi | Raji | Daudi |
| Untreated | 40:1 | 15.6 | 9.6 | | |
| | 20:1 | 0 | 1.3 | | |
| | 10:1 | 8.6 | 4.6 | 0 | 0 |
| | 5:1 | 0 | 2.6 | | |
| | 2.5:1 | 0 | 3.3 | | |
| 0.5 mM PAA | 40:1 | 7.4 | 9.7 | | |
| | 20:1 | 4.5 | 4.3 | | |
| | 10:1 | 0 | 0 | 0 | 0 |
| | 5:1 | 0 | 0 | | |
| | 2.5:1 | 0 | 0 | | |
| 2.5 mM PAA | 40:1 | 23.1 | 13.9 | | |
| | 20:1 | 18.3 | 10.0 | | |
| | 10:1 | 11.6 | 9.2 | 0.9 | 0.1 |
| | 5:1 | 3.6 | 4.0 | | |
| | 2.5:1 | 0 | 0 | | |
| 5 mM PAA | 40:1 | 31.0 | 30.5 | | |
| | 20:1 | 27.0 | 24.2 | | |
| | 10:1 | 16.7 | 15.8 | 1.9 | 2.4 |
| | 5:1 | 6.6 | 10.2 | | |
| | 2.5:1 | 3.5 | 7.1 | | |
| 10 mM PAA | 40:1 | 38.8 | 44.1 | | |
| | 20:1 | 23.6 | 24.2 | | |
| | 10:1 | 19.9 | 20.2 | 2.6 | 5.1 |
| | 5:1 | 14.4 | 12.8 | | |
| | 2.5:1 | 5.5 | 7.3 | | |
| 5 mM PME | 40:1 | 44.4 | 44.8 | | |
| | 20:1 | 30.9 | 39.3 | | |
| | 10:1 | 7.2 | 11.4 | 3.3 | 6.0 |
| | 5:1 | 3.5 | 8.2 | | |
| | 2.5:1 | 3.9 | 6.3 | | |

TABLE 4A

| | Donor 4: Differential Staining | | |
|---|---|---|---|
| Sample | Lymphocytes | Monocytes | Granulocytes |
| Untreated | 54 | 43 | 3 |
| 0.5 mM PAA Treated | 56 | 42 | 2 |
| 2.5 mM PAA Treated | 73 | 25 | 2 |
| 5 mM PAA Treated | 85 | 14 | 1 |
| 10 mM PAA Treated | 83 | 14 | 3 |
| 5 mM PME Treated | 93 | 6 | 1 |

TABLE 4B

| | Donor 4: FACS Analysis | | | |
|---|---|---|---|---|
| SAMPLE | Leu4* | Leu12* | LeuM3* | Leu19* |
| Untreated | nt | nt | nt | nt |
| 0.5 mM PAA Treated | nt | nt | nt | nt |
| 2.5 mM PAA Treated | 63 | 7 | 18 | 7 |
| 5 mM PAA Treated | 62 | 8 | 11 | 12 |
| 10 mM PAA Treated | 71 | 7 | 5 | 10 |
| 5 mM PME Treated | 65 | 9 | 6 | 7 | nt = not tested
Leu4* = T Lymphocytes
Leu12* = B Lymphocytes
LeuM3* = Monocytes
Leu19* = NK cells

TABLE 4C

| | | Donor 4: LAK ACTIVITY | | | |
|---|---|---|---|---|---|
| | E:T | % CYTOLYSIS | | LU30 | |
| SAMPLE | RATIO | RAJI | DAUDI | RAJI | DAUDI |
| UNTREATED | 40:1 | 0 | 7.2 | | |
| | 20:1 | 0 | 1.0 | | |
| | 10:1 | 0 | 1.2 | 0 | 0 |
| | 5:1 | 0 | 0 | | |
| | 2.5:1 | 0 | 0 | | |
| 0.5 mM PAA | 40:1 | 0 | 9.6 | | |
| | 20:1 | 0 | 5.8 | | |
| | 10:1 | 0 | 0 | 0 | 0 |
| | 5:1 | 0 | 0 | | |
| | 2.5:1 | 0 | 0 | | |
| 2.5 mM PAA | 40:1 | 4.2 | 8.3 | | |
| | 20:1 | 0 | 2.7 | | |
| | 10:1 | 0 | 6.2 | 0 | 0 |
| | 5:1 | 0 | 0 | | |
| | 2.5:1 | 0 | 0 | | |
| 5 mM PAA | 40:1 | 17.4 | 21.9 | | |
| | 20:1 | 14.9 | 16.3 | | |
| | 10:1 | 4.3 | 8.1 | 0.2 | 0.6 |
| | 5:1 | 11.5 | 5.2 | | |
| | 2.5:1 | 1.3 | 3.3 | | |
| 10 mM PAA | 40:1 | 34.8 | 42.2 | | |
| | 20:1 | 16.9 | 24.3 | | |
| | 10:1 | 18.3 | 20.0 | 2.6 | 4.9 |
| | 5:1 | 10.3 | 16.3 | | |
| | 2.5:1 | 5.1 | 6.6 | | |
| 5 mM PME | 40:1 | 11.2 | 17.6 | | |
| | 20:1 | 7.6 | 10.2 | | |
| | 10:1 | 0 | 0.9 | 0 | 0.2 |
| | 5:1 | 0 | 0 | | |
| | 2.5:1 | 0 | 1.8 | | |

Example 3

The dependence of LAK cell activation at high cell density on the concentration of PAA used to treat a preparation of human PBMC, collected by leukapheresis, which have an unusually high monocyte count was evaluated. Occasionally healthy donor leukapheresis collections result in high monocyte counts. On the average the count is 15 to 25% of the mononuclear cells. We checked several donor preparations prior to further processing. One preparation, designated donor 5, yielded nearly double the normal count of monocytes. That preparation was then divided and tested for LAK cell activation after exposure to 0, 5, 10, 15, or 20 mM PAA. A control of 5 mM PME was also run (Table 5A). FACS analyses were not available for these samples. As seen in previous experiments, there was excellent reduction in the monocyte counts. 50 mL cultures of the cells in rIL-2-supplemented AIM-V cell culture medium yielded better than 100% of the inoculated cell number. The LAK cell activation again showed a responce related to the concentration of PAA used. Optimal LAK activity was obtained in the sample treated at 10 mM PAA (Table 5B).

TABLE 5A

| | Donor 5: Differential Staining | | |
|---|---|---|---|
| Sample | Lymphocytes | Monocytes | Granulocytes |
| Untreated | 56 | 43 | 1 |
| 5 mM PAA Treated | 91 | 7 | 2 |
| 10 mM PAA Treated | 93 | 3 | 4 |
| 15 mM PAA Treated | 93 | 5 | 2 |
| 20 mM PAA Treated | 93 | 4 | 3 |
| 5 mM PME Treated | 95 | 5 | 0 |

TABLE 5B

Donor 5 LAK Activity
% Cytolysis of Raji Cells

| E:T Ratio | Untreated | [PAA], (mM) | | | | 5 mM PME |
| --- | --- | --- | --- | --- | --- | --- |
| | | 5 | 10 | 15 | 20 | |
| 40:1 | 20.5 | 64.3 | 86.6 | 52.8 | 38.9 | 67.9 |
| 20:1 | 10.5 | 42.3 | 70.8 | 54.4 | 24.9 | 42.9 |
| 10:1 | 46.3 | 23.0 | 33.4 | 41.4 | 33.1 | 24.7 |
| 5:1 | 45.3 | 22.6 | 16.3 | 20.5 | 30.8 | 23.7 |
| 2.5:1 | 12.9 | 19.2 | 4.7 | 8.4 | 24.7 | 42.3 |

TABLE 5C

Donor 5: LAK Activity
% Cytolysis of Raji Cells

| E:T Ratio | Untreated | [PAA] | | | | 5 mM PME |
| --- | --- | --- | --- | --- | --- | --- |
| | | 5 mM | 10 mM | 15 mM | 20 mM | |
| 40:1 | 28.1 | 47.9 | 71.9 | 36.3 | 22.4 | 59.8 |
| 20:1 | 19.5 | 34.4 | 52.6 | 31.7 | 12.1 | 40.7 |
| 10:1 | 29.4 | 15.9 | 18.7 | 21.8 | 19.5 | 23.2 |
| 5:1 | 19.2 | 16.3 | 27.6 | 12.9 | 13.7 | 21.8 |
| 2.5:1 | 14.4 | 15.5 | 3.8 | 3.0 | 10.7 | 21.0 |

Example 4

PBMC were obtained from Biological Specialty (Lansdale, PA) and separated by Ficoll-Paque (Pharmacia, Piscataway, NJ) density gradient sedimentation. PBMC ($1 \times 10^7$ cells/mL) in RPMI-1640 medium, after Ficoll separation, were incubated with freshly prepared PME, PAA, or combinations thereof at room temperature for 40 min. The stock solutions were adjusted to pH 7.4 before the addition to PBMC. The cells were washed with RPMI-1640 medium. Monocyte depletion from PBMC was assessed by Giemsa staining.

The cells were cultured in polypropylene tubes with medium supplemented with 10% fetal calf serum and 400 U/mL of rIL-2 (BRMP units) at a cell density of $1 \times 10^7$ cells/mL, for 4 days at 37° C. After the culture period, the resulting cells were harvested for cytotoxicity assays against $^{51}$Cr-labeled Raji (to measure LAK activity) and K562 (to measure NK activity) target cells. All assays were carried out in triplicate in round bottom microtiter plates in a total volume of 0.2 mL. Labeled target cells in 0.1 mL ($1 \times 10^4$ cells) were added to 0.1 mL of effector cells at various concentrations to obtain appropriate final effector cell:target cell ratios (E:T). The microtiter plates were centrifuged for 3 min at 80 x g and then incubated for 2 hr (NK assay) or 4 hr (LAK assay). Three E:T ratios were assessed. The data shown is with E:T ratio of 20:1 in 2 hr assays for K562 and 4 hr assays for Raji.

PAA was compared with the effects of PME on PBMC to assess their effects on monocyte depletion, NK activity and LAK activation by IL-2. PAA depleted monocytes from PBMC in a dose-dependent manner. The NK activity of PAA- or PME-treated cells was also inhibited before culture (Day 0). The activation of LAK activity by IL-2 was also dependent on the amount of monocytes depleted by PAA or PME. In most of the donors tested, PAA and PME were equally effective at enhancing LAK-cell generation, when used at the optimal concentration (Table 6).

For two of the three donors tested, under the conditions used, the combination of PME and PAA did not show any substantial improvement over the use of 5 mM PME alone (Table 7) although it did show good monocyte depletion and LAK activation. However, for one donor (Exp. 2, Table 7), the combination of PAA and PME appeared to be additive. This result indicates that, at least for some donors, the combination of PAA and PME may result in a greater level of LAK activity than can be obtained using either agent alone.

Each experiment in Tables 6 and 7 ("Exp.") represents a separate set of donor cells.

The results of the foregoing examples demonstrate that monocyte depletion and subsequent LAK cell activation based on pretreating the PBMC with PAA and/or PME is dependent on the donor and as such PAA and/or PME are viable treatment alternatives. If for example, PME is initially used to treat a donor's PBMC and insufficient monocyte depletion results with corresponding insufficient LAK cell activation, the clinician can now turn to PAA or a combination of PAA and PME which may yield sufficient monocyte depletion.

TABLE 6

Effect of PME and PAA on Monocyte Depletion, NK Activity and LAK Activation

| | Day 0 | | Cytolytic Activity Following LAK Activation (Day 3-4) | |
| --- | --- | --- | --- | --- |
| | % Monocytes | NK Activity (K562) | NK (K562) | LAK (Raji) |
| Exp. 1 | | | | |
| Control | 50 | 15.4 | 47.3 ± 1.8 | 3.4 ± 0.4 |
| PAA (5 mM) | 8 | 10.2 | 50.1 ± 0.7 | 8.1 ± 0.6 |
| PME (2.5 mM) | 8 | 8.2 | 58.0 ± 0.5 | 23.8 ± 2.3 |
| Exp. 2 | | | | |
| Control | 33 | | 8.7 ± 0.4 | 16.3 ± 1.3 |
| PAA (5 mM) | 11 | | 40.8 ± 1.3 | 59.3 ± 1.1 |
| PME (5 mM) | 3.5 | | 51.2 ± 0.3 | 60.0 ± 2.3 |
| Exp. 3 | | | | |
| Control | 34 | 21. ± 0.6 | 39.1 ± 1.4 | 18.1 ± 1.0 |
| PAA (1 mM) | 32 | 19.5 ± 0.5 | 45.5 ± 0.5 | 19.8 ± 0.7 |
| PAA (5 mM) | 13 | 8.7 ± 0.6 | 52.6 ± 0.0 | 30.0 ± 1.6 |
| PAA (10 mM) | 8 | 18.1 ± 0.4 | 55.0 ± 1.0 | 36.8 ± 1.5 |
| PME (5 mM) | 1 | 15.1 ± 0.3 | 57.6 ± 6.8 | 44.4 ± 0.6 |
| PME (10 mM) | 2 | 6.4 ± 1.1 | 52.8 ± 1.6 | 36.0 ± 1.0 |
| Exp. 4 | | | | |
| Control | 49.5 | 45.7 ± 1.6 | 46.4 ± 2.1 | 7.4 ± 0.5 |
| PAA (1 mM) | 27.5 | 36.7 ± 1.5 | 48.3 ± 0.7 | 10.3 ± 0.2 |
| PAA (5 mM) | 10.5 | 30.9 ± 1.2 | 49.3 ± 0.9 | 12.7 ± 1.2 |
| PAA (10 mM) | 3 | 20.8 ± 1.0 | 26.7 ± 1.2 | 10.5 ± 0.4 |

TABLE 6-continued

Effect of PME and PAA on Monocyte Depletion, NK Activity and LAK Activation

|  | Day 0 | | Cytolytic Activity Following LAK Activation (Day 3-4) | |
|---|---|---|---|---|
|  | % Monocytes | NK Activity (K562) | NK (K562) | LAK (Raji) |
| PME (5 mM) | 2.5 | 14.4 ± 1.0 | 56.6 ± 1.1 | 33.3 ± 0.3 |
| Exp. 5 | | | | |
| Control | 14.5 | 54.2 ± 1.0 | 14.3 ± 0.6 | 40.0 ± 1.6 |
| PAA (5 mM) | 7 | 41.8 ± 0.7 | 25.6 ± 0.8 | 37.3 ± 0.8 |
| PAA (10 mM) | 1 | 42.0 ± 1.0 | 27.1 ± 0.6 | 50.7 ± 0.7 |
| PME (5 mM) | 6.5 | 46.0 ± 1.0 | 26.5 ± 0.7 | 49.5 ± 1.4 |
| PME (10 mM) | 1 | 33.6 ± 0.6 | 27.6 ± 1.0 | 53.3 ± 0.4 |

TABLE 7

Effect of Combination of PME and PAA on Monocyte Depletion, NK Activity and LAK Activation Exp. 1

| [PME]. (mM) | [PAA]. (mM) | | | |
|---|---|---|---|---|
|  | 0 | 1 | 5 | 10 |
| *% Monocytes (Day 0)* | | | | |
| 0 | 34 | 32 | 13 | 8 |
| 5 | 1 | 3 | 3 | 3.5 |
| 10 | 2 | 2 | 6 | 3 |
| *% Cytotoxicity Against K562 (Day 0)* | | | | |
| 0 | 21 | 19.5 | 8.7 | 8.1 |
| 5 | 15.1 | 13.6 | 13.0 | 11.4 |
| 10 | 6.4 | 10.4 | 10.3 | 8.1 |
| *LAK Activity Against Raji (% Lysis) (Day 3-4)* | | | | |
| 0 | 39.1 | 45.3 | 52.6 | 52.0 |
| 5 | 57.6 | 59.2 | 61.2 | 48.2 |
| 10 | 52.8 | 56.1 | 51.2 | 51.2 |

Exp. 2

| [PME]. (mM) | [PAA]. (mM) | | | |
|---|---|---|---|---|
|  | 0 | 1 | 5 | 10 |
| *% Monocytes (Day 0)* | | | | |
| 0 | 49.5 | 27.5 | 10.5 | 3 |
| 5 | 2.5 | 4.5 | 3 | 4.5 |
| *% Cytotoxicity Against K562 (Day 0)* | | | | |
| 0 | 45.7 | 36.7 | 30.9 | 20.8 |
| 5 | 14.4 | 14.0 | 7.3 | 16.6 |
| *LAK Activity Against Raji (% Lysis) (Day 3-4)* | | | | |
| 0 | 7. | 10.3 | 12.7 | 10.5 |
| 5 | 33.3 | 24.0 | 41.3 | 44.3 |

Exp. 3

| [PME]. (mM) | [PAA]. (mM) | | |
|---|---|---|---|
|  | 0 | 5 | 10 |
| *% Monocytes (Day 0)* | | | |
| 0 | 15 | 7 | 2 |
| 1 | 7 | 1 | 1.5 |
| 5 | 1.5 | 0 | 1 |
| *% Cytotoxicity Against K562 (Day 0)* | | | |
| 0 | 40.6 | 31.3 | 30.5 |
| 1 | 45.1 | 39.7 | 43.7 |
| 5 | 33.5 | 39.9 | 17.8 |
| *LAK Activity Against Raji (% Lysis) (Day 3-4)* | | | |
| 0 | 55.9 | 57.0 | 61.2 |
| 1 | 72.2 | 62.0 | 69.0 |
| 5 | 61.1 | 67.9 | 58.5 |

Example 5

PBMC were treated with PME or various amino acid amides for 40 min at room temperature. Monocyte content was determined by FACS analysis using Leu3 antibody, which is a surface marker for monocytes. NK activity )E:T ratio, 25:1) was measured against K562 cells. LAK activation was determined after the cells were incubated with RPMI-1640 containing 4% human serum, and 400 U/mL rIL-2 (BRMP units) for 3 to 4 days at $1 \times 10^7$ cells/mL, using Raji cells as targets. The results (Table 8) show that the amino acid amide of leucine, isoleucine, valine, as well as phenylalanine are effective at enhancing the level of LAK activity relative to that obtained in the absence of treatment with amino acid amide. Each experiment (Exp.) in table 8 represents a separate set of donor cells.

TABLE 8

|  |  | Day 0 | | Cytolytic Activity Following LAK Activation | |
|---|---|---|---|---|---|
|  |  | % Monocytes | NK Activity | NK (K562) | LAK (Raji) |
| Exp. 1 | | | | | |
| 0 |  | 23 | 50 | 15 | 3 |
| PME. | 5 mM | 0 | 5 | 64 | 56 |
| TyrNH$_2$. | 5 mM | 25 | 54 | 18 | 5 |
|  | 10 mM | 32 | 70 | 9 | 2 |
| LeuNH$_2$. | 5 mM | 1 | 50 | 54 | 28 |
|  | 10 mM | 0 | 47 | 64 | 48 |
| Exp. 2 | | | | | |
| 0 |  | 12 | 25 | 46 | 14 |
| PME. | 5 mM | 2 | 15 | 61 | 32 |
| PheNH$_2$. | 5 mM | 2 | 34 | 62 | 35 |
| LME. | 5 mM | 1 | 0 | 4 | 5 |
| LeuNH$_2$. | 5 mM | 0 | 35 | 59 | 27 |
| Exp. 3 | | | | | |
| 0 |  | 18 | 54 | 22 | 3 |
| ValNH$_2$, | 5 mM | 16 | 48 | 30 | 10 |
| GluNH$_2$. | 5 mm | 24 | 60 | 19 | 3 |
| AspNH$_2$. | 5 mm | 26 | 61 | 20 | 5 |
| IleNH$_2$. | 5 mm | 6 | 51 | 55 | 17 |
| PME. | 5 mm | 3 | 42 | 67 | 22 |

We claim:

1. In a process for preparing lymphokine-activated killer cells wherein peripheral blood mononuclear cells are cultured to produce a population of cells which when activated with a lymphokine are cytotoxic for natural killer cell-resistant tumor cells, the improvement comprising contacting said peripheral blood mononuclear cells or peripheral blood lymphocytes resulting therefrom with an L-amino acid amide, wherein the L-amino acid is selected for the group consisting of leucine, isoleucine, phenylalanine, and valine, or a mixture of any of the foregoing, and thereafter culturing the resulting cells.

2. A process according to claim 1 wherein said peripheral blood mononuclear cells are human cells.

3. A process according to claim 2 wherein the contacting is performed for a period of about 40 minutes.

4. A process according to claim 3 wherein the amino acid amide is phenylalanine.

5. A process according to claim 4 wherein the phenylalanine amide is present in a concentration of about 1 to 10 mM.

6. A process according to claim 5 wherein the phenylalanine amide is present in a concentration of about 10 mM.

7. A process according to claim 3 wherein the human peripheral blood mononuclear cells or peripheral blood lymphocytes resulting therefrom are cultured in the presence of interleukin-2.

8. A process according to claim 5 wherein the human peripheral blood mononuclear cells or peripheral blood lymphocytes resulting therefrom are cultured in the presence of interleukin-2.

9. A process according to claim 7 wherein the human peripheral blood lymphocytes obtained by contacting with the amino acid amide are washed and resuspended.

10. A process according to claim 8 wherein the human peripheral blood lymphocytes obtained by contacting with phenylalanine amide are washed and resuspended.

11. A process according to claim 9 wherein the resuspended human peripheral blood lymphocytes are cultured for 2 to 4 days in the presence of recombinant interleukin-2.

12. A process according to claim 10 wherein the resuspended human peripheral blood lymphocytes are cultured for 2 to 4 days in the presence of recombinant interleukin-2.

13. A process according to claim 11 wherein the concentration of human peripheral blood lymphocytes is from about $3 \times 10^6$ cells/mL to about $1 \times 10^8$ cells/mL.

14. A process according to claim 12 wherein the concentration of human peripheral blood lymphocytes is from about $3 \times 10^6$ cells/mL to about $1 \times 10^8$ cells/mL.

15. In a process for preparing lymphokine-activated killer cells wherein peripheral blood mononuclear cells are cultured to produce a population of cells which when activated with a lymphokine are cytotoxic for natural killer cell-resistant tumor cells, the improvement comprising contacting said peripheral blood mononuclear cells or peripheral blood lymphocytes resulting therefrom with a combination of an L-amino acid amide and an L-amino acid lower alkyl ester, wherein the L-amino acid amide is selected from the group consisting of leucine, isoleucine, phenylalanine, and valine, and the L-amino acid lower alkyl ester is selected from the group consisting of alanine, aspartic acid, cysteine, glutamic acid, glutamine, phenylalanine, proline, tyrosine, tryptophan, and valine, and thereafter culturing the resulting cells.

16. A process according to claim 15 wherein the peripheral blood mononuclear cells are human.

17. A process according to claim 16 wherein the contacting is performed for a period of about 20 to 40 minutes.

18. A process according to claim 17 wherein the L-amino acid amide is phenylalanine.

19. A process according to claim 18 wherein the ester is L-phenylalanine methyl ester and the amide is phenylalanine amide.

20. A process according to claim 19 wherein the ester is present in a concentration of about 1–5 mM and the amide is present in a concentration of about 1–10 mM.

21. A process according to claim 20 wherein the hydrogen chloride salt of the ester and the amide is present.

22. A process according to claim 19 wherein the human peripheral blood mononuclear cells or peripheral blood lymphocytes are cultured in the presence of interleukin-2.

23. A process according to claim 20 wherein the human peripheral blood mononuclear cells or peripheral blood lymphocytes are cultured in the presence of interleukin-2.

24. A process according to claim 22 wherein the peripheral blood lymphocytes obtained by contacting with the ester and amide are washed and resuspended.

25. A process according to claim 23 wherein the peripheral blood lymphocytes obtained by contacting the ester and amide are washed and resuspended.

26. A process according to claim 24 wherein the resuspended peripheral blood lymphocytes are cultured for 2–4 days in the presence of recombinant interleukin-2.

27. A process according to claim 25 wherein the resuspended peripheral blood lymphocites are cultured for 2–4 days in the presence of recombinant interleukin-2.

28. A process according to claim 26 wherein the concentration of peripheral blood lymphocytes is from about $3 \times 10^6$ cells/mL to about $1 \times 10^8$ cells/mL.

29. A process according to claim 27 wherein the concentration of peripheral blood lymphocytes is from about $3 \times 10^6$ cells/mL to about $1 \times 10^8$ cells/mL.

* * * * *

UNITED STATES PATENT AND TRADEMARK OFFICE
CERTIFICATE OF CORRECTION

PATENT NO. : 5,108,760

DATED : April 28, 1992

INVENTOR(S) : Joseph D. IRR ET AL

Page 1 of 2

It is certified that error appears in the above-identified patent and that said Letters Patent is hereby corrected as shown below:

On title page, item [54], delete "ENHANCES" and insert --ENHANCED--

Item [57], line 4, after "yield" insert --monocyte--

In Column 1, line 1, delete "ENHANCES" and insert -- ENHANCED --.

In Column 1, line 24, delete "mice" and insert -- mice, --.

In Column 1, line 30, delete "316:889-897:" and insert -- 316:889-897 --.

In Column 1, line 31, delete "4,690.915" and insert -- 4,690,915 --.

In Column 1, line 52, delete "4,849,329" and insert -- 4,849,329, --.

In Column 2, line 4, delete "82:2468-2472:" and insert -- 82:2468-2472; --.

In Column 2, line 8, delete "Proc. Acad. Sci. USA" and insert -- Proc. Acad. Sci. USA --.

UNITED STATES PATENT AND TRADEMARK OFFICE
CERTIFICATE OF CORRECTION

PATENT NO. : 5,108,760

DATED : April 28, 1992

INVENTOR(S) : Joseph D. IRR ET AL

It is certified that error appears in the above-identified patent and that said Letters Patent is hereby corrected as shown below:

In Column 2, line 18, after "4,849,329." and before "A", begin a new paragraph.

In Column 3, line 49, after "patent", insert -- application 87107755.8, published December 2, 1987 and --.

In Column 5, before "mM", insert -- 5 --.

In Column 6, line 53, delete "nM" and insert -- mM --.

In Column 6, line 61, delete "nM" and insert -- mM --.

In Column 13, line 66, delete "activity )" and insert --(activity --.

Signed and Sealed this

Twenty-second Day of March, 1994

*Attest:*

BRUCE LEHMAN

*Attesting Officer*     *Commissioner of Patents and Trademarks*